(12) United States Patent
Martin et al.

(10) Patent No.: US 11,798,160 B2
(45) Date of Patent: Oct. 24, 2023

(54) INTEGRATED METHOD FOR CANCER SCREENING

(71) Applicant: Siemens Healthcare GmbH, Erlangen (DE)

(72) Inventors: Raimund Martin, Eggolsheim/Bammersdorf (DE); Wieland Voigt, Moehrendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 107 days.

(21) Appl. No.: 17/047,115

(22) PCT Filed: Mar. 7, 2019

(86) PCT No.: PCT/EP2019/055643
§ 371 (c)(1),
(2) Date: Oct. 13, 2020

(87) PCT Pub. No.: WO2019/201505
PCT Pub. Date: Oct. 24, 2019

(65) Prior Publication Data
US 2021/0201480 A1    Jul. 1, 2021

(30) Foreign Application Priority Data
Apr. 16, 2018 (EP) .................................. 18167453

(51) Int. Cl.
*G06T 7/00* (2017.01)
*G16H 50/20* (2018.01)
(Continued)

(52) U.S. Cl.
CPC ............ *G06T 7/0012* (2013.01); *A61B 5/055* (2013.01); *A61B 5/742* (2013.01); *G16H 30/40* (2018.01);
(Continued)

(58) Field of Classification Search
CPC ......... G06T 7/0012; G06T 2207/10081; G06T 2207/10088; G06T 2207/20084;
(Continued)

(56) References Cited

U.S. PATENT DOCUMENTS

| 6,560,480 B1 * | 5/2003 | Nachaliel | A61B 5/6848 600/547 |
| 8,355,928 B2 * | 1/2013 | Spahn | G16H 40/63 382/128 |

(Continued)

FOREIGN PATENT DOCUMENTS

WO    WO-2009/050676 A1    4/2009

OTHER PUBLICATIONS

International Search Report PCT/ISA/210 for International Application No. PCT/EP2019/055643 dated Jun. 5, 2019.
(Continued)

*Primary Examiner* — Amandeep Saini
*Assistant Examiner* — Julius Chai
(74) *Attorney, Agent, or Firm* — Harness, Dickey & Pierce, P.L.C.

(57) ABSTRACT

A method of screening for a cancer in a patient, an integrated method of screening for a cancer in a patient, a computer program product for carrying out the methods, as well as a medical imaging apparatus for carrying out the methods are disclosed. Based upon the above, it is possible that the patient will obtain a more reliable result from a first medical imaging treatment.

20 Claims, 6 Drawing Sheets

(51) Int. Cl.
  *G16H 30/40* (2018.01)
  *A61B 5/055* (2006.01)
  *A61B 5/00* (2006.01)
(52) U.S. Cl.
  CPC ... *G16H 50/20* (2018.01); *G06T 2207/10081* (2013.01); *G06T 2207/10088* (2013.01); *G06T 2207/20084* (2013.01); *G06T 2207/30096* (2013.01)
(58) Field of Classification Search
  CPC .......... G06T 2207/30096; G16H 50/20; G16H 50/30; G16H 50/70; G16H 30/40; G16H 10/60; A61B 5/055; A61B 5/742
  See application file for complete search history.

(56) References Cited

U.S. PATENT DOCUMENTS

| | | | | |
|---|---|---|---|---|
| 8,529,446 | B2* | 9/2013 | Schmidt | G16H 10/60 706/45 |
| 10,176,896 | B2* | 1/2019 | Sharma | G16H 50/70 |
| 2005/0010098 | A1* | 1/2005 | Frigstad | A61B 6/00 600/407 |
| 2005/0049497 | A1* | 3/2005 | Krishnan | G16H 50/20 600/437 |
| 2007/0021977 | A1* | 1/2007 | Elsholz | G06Q 40/08 705/2 |
| 2007/0239491 | A1 | 10/2007 | Rao et al. | |
| 2008/0113440 | A1* | 5/2008 | Gurney | G01N 1/312 422/65 |
| 2008/0312959 | A1* | 12/2008 | Rose | G16H 10/60 705/2 |
| 2009/0018867 | A1* | 1/2009 | Reiner | G06F 3/04883 705/2 |
| 2009/0067693 | A1* | 3/2009 | Shinagawa | G06T 7/0012 382/128 |
| 2011/0071850 | A1* | 3/2011 | Nuthi | G16Z 99/00 705/3 |
| 2012/0016691 | A1* | 1/2012 | Sievenpiper | G16H 40/20 705/2 |
| 2013/0226621 | A1* | 8/2013 | Van Der Zaag | G16H 40/20 702/19 |
| 2013/0315466 | A1* | 11/2013 | Drell | G06V 20/69 382/133 |
| 2017/0067922 | A1* | 3/2017 | Antoni | G01N 35/1072 |
| 2018/0190384 | A1* | 7/2018 | Shohat | G16H 10/40 |
| 2019/0035501 | A1* | 1/2019 | Zhang | G16H 80/00 |
| 2019/0071795 | A1* | 3/2019 | Nerenberg | C40B 40/06 |
| 2019/0189264 | A1* | 6/2019 | Stoval, III | G16H 30/40 |
| 2019/0380782 | A1* | 12/2019 | McAfee | G16H 30/40 |

OTHER PUBLICATIONS

Written Opinion PCT/ISA/237 for International Application No. PCT/EP2019/055643 dated Jun. 5, 2019.
European Search Report for European Application No. 18167453.2 dated Oct. 22, 2018.
European Office Action for European Application No. 18167453.2 dated Oct. 6, 2020.
Liu et al., "Radiologic Features of Small Pulmonary Nodules and Lung Cancer Risk in the National Lung Screening Trial: A Nested Case-Control Study", Radiology: vol. 000: No. 0, p. 1-9, 2018.
Wilson et al., "Radiomics of Pulmonary Nodules and Lung Cancer", Translation Lung Cancer Research, 2017; 6(1):86-91.
Hawkins et al. "Predicting Malignant Nodules from Screening CT Scans", Journal of Thoracic Oncology, vol. 11 No 12: 2120-2128, Dec. 2016.

* cited by examiner

INTEGRATED METHOD FOR CANCER SCREENING

PRIORITY STATEMENT

This application is the national phase under 35 U.S.C. § 371 of PCT International Application No. PCT/EP2019/055643 which has an International filing date of Mar. 7, 2019, which designated the United States of America and which claims priority to European application no. EP18167453.2 filed Apr. 16, 2018, the entire contents of each of which are hereby incorporated by reference herein, in their entirety and for all purposes.

FIELD

Embodiments of the disclosure generally relates to a method of screening for a cancer in a patient, an integrated method of screening for a cancer in a patient, a computer program product for carrying out the methods, as well as a medical imaging apparatus for carrying out the methods With embodiments of the present application it is possible that the patient will obtain a more reliable result from a first medical imaging treatment.

BACKGROUND

Today's methods for cancer screening suffer from the problem of limited sensitivity and/or specificity, leading to either false negative results (persons that have cancer are not detected) or to false positive results (healthy persons are undergoing unnecessary follow up procedures).

Screening candidates are usually pre-selected based on certain risk factors (e.g. years of tobacco smoking, age) and it is tolerated that other persons are excluded from the screening program to limit cost or—alternatively—cost and side effects of unnecessary follow-up procedures are accepted.

SUMMARY

The inventors discovered that these limitations lead to low acceptance of screening programs.

The inventors discovered that there thus is a need for improved methods of screening for cancer in a patient, which have improved sensitivity and specificity and particularly can be carried out in a short time frame.

The present inventors found that integrating several diagnostic methods in combination with automated computer based analysis and decision support in real time—to select and execute only those diagnostic steps that are necessary—pro-vide a physician all the information required to perform a reliable diagnosis.

In a first embodiment, the present invention relates to a method of screening for a cancer in a patient, comprising:

obtaining or providing in a first step at least one first image of a tissue of the patient suspected of being carcinogenic using medical imaging in a first medical imaging apparatus;

automated determination of a first set of parameters from the at least one first image;

automated determination whether a subsequent screening step should be carried out based on the first set of parameters; and automated display of a recommendation whether the subsequent screening step should be carried out, preferably in a first display unit, wherein the automated display of a recommendation whether the subsequent screening step should be carried out takes place within 15 minutes after the step of obtaining or providing the at least one first image of a tissue of the patient.

Furthermore disclosed is in a second embodiment, a method, particularly an integrated method, of screening for a cancer in a patient, comprising:

obtaining or providing in a first step at least one first image of a tissue of the patient suspected of being carcinogenic using medical imaging in a first medical imaging apparatus;

automated determination of a first set of parameters from the at least one first image;

automated selection of a recommended subsequent screening step based on the first set of parameters;

automated display of the recommended subsequent screening step; and optionally carrying out the recommended subsequent screening step.

A further embodiment of the invention is directed to a computer program product comprising computer executable instructions which, when executed, perform a method according to the first and/or second embodiment.

Also disclosed is a medical imaging apparatus in one embodiment, comprising:

means for obtaining at least one first image of a tissue of a patient; and means for analyzing the at least one image of a tissue of a patient, including an automated determination of a first set of parameters from the at least one first image, wherein also an automated determination whether a subsequent screening step should be carried out based on the first set of parameters is carried out; and means for displaying results of the analyzation of the at least one image of a tissue of a patient;

further comprising:

means for displaying the result of the automated determination whether a subsequent screening step should be carried out based on the first set of parameters.

Further aspects and embodiments of the invention are disclosed in the claims and can be taken from the following description, figures and examples, without being limited thereto.

BRIEF DESCRIPTION OF THE DRAWINGS

The enclosed drawings should illustrate embodiments of the present invention and convey a further understanding thereof. In connection with the description they serve as explanation of concepts and principles of the invention. Other embodiments and many of the stated advantages can be derived in relation to the drawings. The elements of the drawings are not necessarily to scale towards each other. Identical, function ally equivalent and acting equal features and components are denoted in the figures of the drawings with the same reference numbers, unless noted otherwise.

DETAILED DESCRIPTION OF THE EXAMPLE EMBODIMENTS

Definitions

Figure 1:
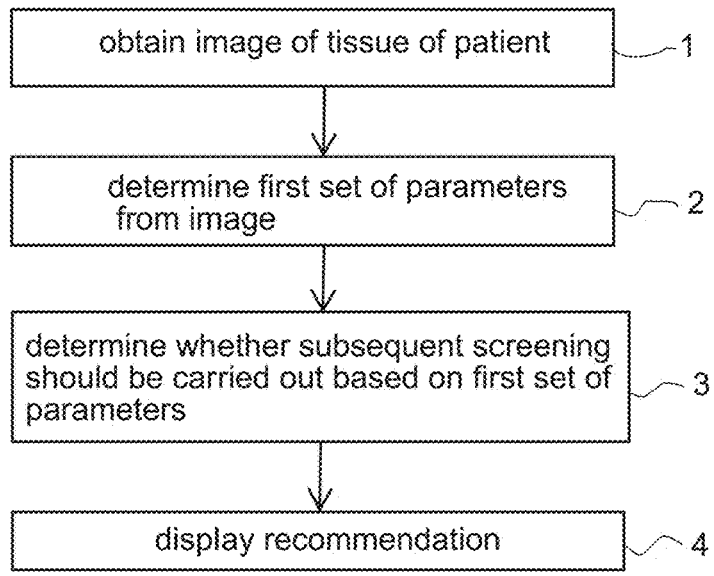
FIGS. 1 to 4 show schematically steps in a method of the first embodiment of the invention.

Unless defined otherwise, technical and scientific terms used herein have the same meaning as commonly understood by one of ordinary skill in the art to which this invention belongs.

In the context of the present invention a "sample" of a patient is not particularly restricted, as long as it can be further analyzed. Examples for samples are: cells, tissue, biopsy specimens, body fluids, e.g. blood, urine, saliva, sputum, plasma, serum, cell culture supernatant, swab sample and others. Preferred in the present invention are fluid samples like body fluids, particularly blood.

According to certain embodiments, the patient in the present methods is a vertebrate, more preferably a mammal and most preferred a human patient.

A vertebrate within the present invention refers to animals having a vertebrae, which includes mammals—including humans, birds, reptiles, amphibians and fishes. The present invention thus is not only suitable for human medicine, but al so for veterinary medicine. Computed tomography (CT) scanning combines x-ray imaging with sophisticated computer analysis to usually produce multiple, cross-sectional images, e.g. of the inside of parts of or the whole of a body of a patient. Low-dose CT or LDCT uses less ionizing radiation than a conventional CT scan. The dose thereby can depend e.g. on the tissue to be scanned, the location thereof, etc. For example, a low-dose CT of the lung can be carried out with about 1 to 3 mSv, e.g. about 2 mSv, per scan, compared to the usual, normal about 6 mSv per scan in a normal CT.

The type of cancer in the present application is not particularly restricted and includes any type of cancer that can be present in the patient. Preferably the cancer is a cancer that can be easily visualized and/or localized using a first medical imaging apparatus, e.g. lung cancer, breast cancer, liver cancer, prostate cancer, pancreatic cancer, brain tumors, sarcoma etc.

In the present invention the first step of obtaining or providing at least one first image of a tissue of the patient suspected of being carcinogenic using medical imaging in a first medical imaging apparatus is also referred to as first medical imaging step (or first imaging step) in the following.

Before the invention is described in example detail, it is to be understood that this invention is not limited to the particular component parts of the process steps of the methods described herein as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. For example, the term "a" as used herein can be understood as one single entity or in the meaning of "one or more" entities. It is al so to be understood that plural forms include singular and/or plural referents unless the context clearly dictates otherwise. It is moreover to be understood that, in case parameter ranges are given which are delimited by numeric values, the ranges are deemed to include these limitation values.

A first embodiment of the present invention relates to a method of screening for a cancer in a patient, comprising:

obtaining or providing in a first step at least one first image of a tissue of the patient suspected of being carcinogenic using medical imaging in a first medical imaging apparatus;

automated determination of a first set of parameters from the at least one first image;

automated determination whether a subsequent screening step should be carried out based on the first set of parameters; and automated display of a recommendation whether the subsequent screening step should be carried out, preferably in a first display unit, wherein the automated display of a recommendation whether the subsequent screening step should be carried out takes place within 15 minutes after the step of obtaining or providing the at least one first image of a tissue of the patient.

According to certain embodiments, the steps are carried out in the sequence given.

With this method particularly an early determination whether a subsequent screening step with a follow-up diagnosis is needed is possible, so that the subsequent screening step can be carried out, if necessary, while the patient is still present at the facility where at least one first image of a tissue of the patient suspected of being carcinogenic using medical imaging in a first medical imaging apparatus is obtained. This provides the person analyzing this information, e.g. a doctor, a tool for deciding whether such subsequent screening step is necessary, without letting the patient wait for the final diagnosis of the at least one first image of a tissue of the patient suspected of being carcinogenic using medical imaging in a first medical imaging apparatus.

This way the number of early unclear diagnoses or even misdiagnoses can be reduced, while at the same time also a fast diagnosis from a subsequent screening step can be obtained, if necessary, so that the patient will obtain a final diagnosis faster.

Of course, it is also possible that no subsequent screening step is necessary. In this case the method of the first aspect nevertheless provides the person giving a final diagnosis, e.g. a doctor, a possibility to clarify this outcome at an early stage, so that it may not be necessary that the patient returns for a subsequent screening or a later meeting with the doctor, while at the same time providing the patient with an early diagnosis with sufficient sensitivity and specificity, even if the whole data from the obtaining or providing in a first step at least one first image of a tissue of the patient suspected of being carcinogenic using medical imaging in a first medical imaging apparatus is not fully analyzed and/or read by the person making the final diagnosis, e.g. a doctor.

The obtaining or providing in a first step at least one first image of a tissue of the patient suspected of being carcinogenic using medical imaging in a first medical imaging apparatus is not particularly restricted. Particularly this step is non-invasive. In the present method also more than one image can be obtained in the first step, e.g. a multitude of images.

The medical imaging apparatus is therein not particularly restricted and those used for medical imaging can be applied, e.g. a computer tomography (CT) device, e.g. a computer tomography scanner, e.g. a low-dose computer tomograph, a magnetic resonance imaging (MRI) device like a magnetic resonance tomograph (MRT) device, a positron emission tomography (PET) device, e.g. a PET/CT or PET/MRT device, which can be used to scan a part of the body of a patient or used for a full body screening. The medical imaging apparatus as well as the method of obtaining or providing at least one first image with it can thereby be adapted to a specific diagnosis or expected diagnosis, e.g. for lung cancer screening with CT, breast cancer using MRI, etc. Also, it is not excluded that the first image is provided from a measurement that was intended for a different purpose, e.g. during trauma imaging, e.g. after an accident, etc.

According to certain embodiments, the at least one first image of a tissue of the patient suspected of being carcinogenic using medical imaging in a first medical imaging apparatus is obtained using a computed tomography scan and/or using magnetic resonance imaging, particularly low-dose computer tomography or even ultralow-dose computer tomography.

Again, the doses can depend e.g. on the tissue to be scanned, its location, etc. For example, a low-dose CT of the lung can be carried out with about 1 to 3 mSv, e.g. about 2 mSv, per scan, compared to the usual, normal about 6 mSv per scan in a normal CT. An ultralow-dose CT of the lung can even be carried out with about 0.5 mSv or less, particularly less than 0.5 mSv.

Particularly the present method is suitable for low-cost medical imaging methods with reduced sensitivity and/or specificity. For example, a CT measurement can be carried out as a first medical imaging step for e.g. a lung cancer, whereas a MRI based method can be used for e.g. breast cancer. Therefore, the present method can be e.g. directed to a screening for lung cancer, wherein in the first step a CT measurement device is used, and/or directed to a screening for breast cancer, wherein in the first step a MRI based measurement de vice is used.

Furthermore, the automated determination of a first set of parameters from the at least one first image is not particularly restricted, as long as it is carried out automatically. In this regard any suitable means can be used for the automated determination, e.g. suitable, e.g. computing, means that analyze the at least one first image, which can be integrated in the first medical imaging apparatus and/or can be located externally. Preferably, the means for analyzing the at least one image of a tissue of a patient, including an automated determination of a first set of parameters from the at least one first image, wherein also an automated determination whether a subsequent screening step should be carried out based on the first set of parameters is carried out, are located in the first medical imaging apparatus. The means, particularly computing means, are not particularly restricted and can contain suitable algorithms for analyzing and evaluating the at least one first image of a tissue of the patient. According to certain embodiments, the means can include machine learning tools, e.g. neural networks, deep learning, etc.

The analysis of the image in the automated determination of a first set of parameters is not particularly restricted. Several considerations can be taken into account for the analysis of the image, e.g. the location and/or size of tissue suspected of being carcinogenic, the shape of such a tissue, the texture of the tissue, the presence of further suspect tissue, e.g. metastases, the presence of features in the tissue like fringes, etc. For example, such parameters are readily known for studying lung cancer, where factors like roundness, the presence of fringes as example texture parameters, size, etc. are routinely considered.

Also, the automated determination of a first set of parameters can be carried out using additionally reference data, e.g. from other comparable images, e.g. the same body part, of other individuals, being recorded with the same first medical imaging apparatus and/or other medical imaging apparatuses delivering comparable results, e.g. of the same type.

The reference data can be from the patient that is screened, if available, and include data like age, smoking status, data on alcohol and/or drug abuse, height, weight, genetic risks, etc., as well as from other patients, like similar observations, similar risk group, etc., and they can be e.g. provided from a suitable database. Suitable determination methods for such a first set of parameters that can discriminate whether a cancer may be present in the patient based on the at least one first image can be chosen by the skilled person based on the type of image provided, the cancer that is screened for, etc., and may vary according to the tissue to be screened, the first medical imaging apparatus applied, etc. General statistical analysis methods like the determination of ROC (Receiver Operating Characteristic) curves, etc. can be carried out in the automated determination of a first set of parameters.

According to certain embodiments, the automated determination of a first set of parameters from the at least one first image is carried out in or in the vicinity of the first medical imaging apparatus.

The first set of parameters is not particularly restricted and may depend on the type of cancer screened. It can involve any data that can be obtained from analysis of the at least one first image of a tissue of the patient, which is not particularly restricted. Examples thereof include location, size, shape, texture, etc. of a tissue suspected of being carcinogenic.

Also, the automated determination whether a subsequent screening step should be carried out based on the first set of parameters is not particularly restricted. Again, it is possible that the first set of parameters is compared therein to reference data, e.g. from the same patient that is screened for cancer, e.g. from an earlier screening, and/or from other patients that have and/or have not a cancer, e.g. in the same tissue that is screened.

According to certain embodiments, the automated determination whether a subsequent screening step should be carried out based on the first set of parameters can be based on a certain probability that a cancer, e.g. malignant tumor, is present in the at least one first image of a tissue of the patient, wherein the probability can be determined by suitable methods, e.g. statistical analysis, comparison to reference data, etc. For determining a value of a probability that is sufficiently high for giving a recommendation that the subsequent screening step should be carried out, different aspects can be taken into account, e.g. the usual specificity and/or sensitivity of the first step using the first medical imaging apparatus, patient data, data from other patients, etc. The probability of the presence of a cancer can be e.g. calculated in the determination of a first set of parameters from the at least one first image based on different parameters in the image, e.g. size of tissue suspected of being malignant, location thereof, texture of the tissue, etc., and can be e.g. dependent on the type of cancer.

Furthermore, the automated display of a recommendation whether the subsequent screening step should be carried out, preferably in a first display unit, is not particularly restricted. The automated display can occur in a part of the first medical imaging apparatus, a separate device, a suitable display unit, etc. According to certain embodiments, the automated display of a recommendation whether the subsequent screening step should be carried out occurs in a first display unit that can be connected to the first medical imaging apparatus or can be separate thereof. It is particularly useful if the recommendation is displayed in a separate device, e.g. e separate first display unit, and/or is forwarded to a separate device where a doctor that can or should analyze the at least one first image of a tissue of the patient can obtain the result of the recommendation quickly, e.g. even without entering the room where the first medical imaging apparatus is located, so that the doctor can quickly decide whether a subsequent screening step should be carried out.

In this regard it is also possible that a person different from the doctor gets notified by the automated display of the recommendation, which in turn can notify a doctor that can or should analyze the at least one first image of a tissue of the patient so that the doctor then can decide whether to recommend a subsequent screening step or not. For this recommendation of course the doctor can also consider the first set of parameters provided in the present method and/or the at least one first image obtained or provide.

Thus, according to certain embodiments, the present method also comprises an automated display of the at least one first image of a tissue of the patient and/or the fir automated display of the at least one first image of a tissue of the patient and/or the first set of parameters automatically determined. This automated display of the at least one first image of a tissue of the patient and/or the first set of parameters automatically determined can be combined together with the automated display of a recommendation whether the subsequent screening step should be carried out or not.

In the present method of the first embodiment the automated display of a recommendation whether the subsequent screening step should be carried out takes place within 15 minutes, preferably within 10 minutes, further preferably within 5 minutes, even further preferably within 2 minutes, particularly preferably within 1 minute after the step of obtaining or providing the at least one first image of a tissue of the patient. In this regard it is particularly preferably that the recommendation whether a subsequent screening step is carried out is made available as fast as possible so that a doctor or another person with similar function can then decide whether the subsequent screening step is actually carried out, so that it can be carried out quickly after the obtaining of providing of the at least one first image, i.e. preferably while the patient that was screened is still present at a doctor's office and/or hospital, so that the subsequent screening step can be carried out directly thereafter, if necessary.

According to certain aspects, the method further comprises: an automated selection of a recommended subsequent screening step based on the first set of parameters; an automated display of the recommended subsequent screening step; and optionally carrying out the recommended subsequent screening step.

In these aspects and embodiments, the automated selection of a recommended subsequent screening step based on the first set of parameters and/or the automated display of the recommended subsequent screening step are not particularly restricted.

Herein the automated selection of a recommended subsequent screening step based on the first set of parameters is not particularly restricted. While it is also possible that more than one subsequent screening step is recommended, according to certain embodiments only one subsequent screening step is recommended based on the first set of parameters. Particularly, the subsequent screening step can also be suitably adapted to the patient, e.g. based on patient data.

The subsequent screening step is not particularly restricted, as long as it enables a further clarification of a cancer in a patient. At this stage it may also be possible to look for more than one cancer, e.g. if the first set of parameters gives a recommendation in this regard. Example subsequent screening steps will be given below, and can involve e.g. analyzing a sample from a patient that is to be obtained or has already been obtained before, e.g. in a liquid biopsy, e.g. a blood sample, and/or carrying out a second medical imaging step in a second medical imaging apparatus that can be the same as the first medical imaging apparatus or different.

Also, the automated display of the recommended subsequent screening step can be together with the automated display of the at least one first image of a tissue of the patient and/or the first set of parameters automatically determined and/or the automated display of a recommendation whether the subsequent screening step should be carried out or not, although the recommended subsequent screening step of course should be based on a recommendation that the subsequent screening step is carried out. However, the automated display of the recommended subsequent screening step can also be separate from either of these or all of these other displays.

The automated display of the recommended subsequent screening step is preferably occurring in about the same time frame as the automated display of a recommendation whether the subsequent screening step should be carried out, or at least in a time frame that is not particularly longer. The automated display of the recommended subsequent screening step preferably takes place within 15 minutes, preferably within 10 minutes, further preferably within 5 minutes, even further preferably within 2 minutes, particularly preferably within 1 minute after the step of obtaining or providing the at least one first image of a tissue of the patient. Again it is particularly preferably that the recommendation for the subsequent screening step—if it is carried out—is made available as fast as possible so that a doctor or another person with similar function can then decide whether this subsequent screening step is actually carried out, so that it can be carried out quickly after the obtaining of providing of the at least one first image, i.e. preferably while the patient that was screened is still present at a doctor's office and/or a hospital, so that the subsequent screening step can be carried out directly thereafter, if necessary.

However, it is also possible that the automated display of the recommended subsequent screening step is not leading to the carrying out of the subsequent screening step shortly thereafter. It is also possible that the recommended subsequent screening step is actually a further monitoring of the tissue, e.g. again with the first medical imaging apparatus, after a sufficient time, e.g. a few days, weeks, or months, depending on the type of cancer suspected.

If the subsequent screening step is carried out shortly after the recommendation of the subsequent screening step, it is preferred that it is carried out on the same day when or at least within a few days after the least one first image of a tissue of the patient suspected of being carcinogenic using medical imaging in a first medical imaging apparatus is obtained or provided. At least parts thereof, e.g. the taking of a sample and/or the taking of at least one second image in a second medical imaging apparatus—which can be the same or different as the first medical imaging apparatus is then preferably carried out within 4 hours, preferably less than 3 hours, preferably within 2 hours, further preferably within 1 hour, further preferably within less than 1 hour, more preferably within 30 minutes, after the at least one first image of a tissue of the patient suspected of being carcinogenic using medical imaging in a first medical imaging apparatus is obtained or provided. According to certain embodiments, the recommended subsequent screening step is carried out within 4 hours, preferably less than 3 hours, preferably within hours, further preferably within 1 hour, further preferably within less than 1 hour, more preferably within 30 minutes, after the first step. Particularly this is useful if further interaction is required from the patient, e.g. by obtaining or providing a sample, preferably a liquid sample, e.g. a blood sample, and/or if a further screening using a second medical imaging apparatus, which can be the same as the first imaging apparatus or be different, is carried out, wherein it is even possible that the patient may have to take a compound like a contrasting agent for improved imaging.

The optional carrying out the recommended subsequent screening step is not particularly restricted, but is preferably essentially non-invasive, further preferably non-invasive. It can encompass taking a sample from the patient, though, which can be done by routine measures that can be carried out in the absence of a doctor, e.g. a standard method of taking a blood sample, taking a sample of urine, etc., and/or encompass the patient taking one or more compounds for improved imaging in the subsequent screening step, e.g. a contrasting agent for improved imaging, which can be suitably selected and is not particularly limited. With regard to the choice of the subsequent screening step, also further data, e.g. further patient data, can be taken into account, e.g. whether a patient is allergic to a certain compound to be taken and/or whether a patient is not fit for a specific screening method.

According to certain embodiment, the method further comprises an automated generation of a first set of criteria for the recommended subsequent screening step using the first set of parameters; and optionally carrying out the recommended subsequent screening step using the first set of criteria.

Also in this regard the automated generation of a first set of criteria for the recommended subsequent screening step using the first set of parameters is not particularly limited, and again can involve using suitable computing devices/ methods, e.g. including machine learning tools, as well as using further data, e.g. patient data and/or further reference data. The first set of criteria can then again be automatically displayed and/or automatically applied in the subsequent screening step, and can involve data like analyzing steps and/or agents to be used on a sample of the patient, and/or settings for a subsequent, second medical imaging step.

In this regard also the subsequent screening step, e.g. a liquid biopsy and/or a further, second medical imaging step, and/or the first set of criteria can be adapted with regard to the sensitivity and/or specificity that is to be obtained, also in view of the results obtained in the first medical imaging step.

Furthermore, the optional carrying out the recommended subsequent screening step using the first set of criteria is not particularly restricted, but is preferably essentially non-invasive, further preferably non-invasive. It can again encompass taking a sample from the patient, which can be done by routine measures that can be carried out in the absence of a doctor, e.g. a standard method of taking a blood sample, taking a sample of urine, etc., and/or encompass the patient taking one or more compounds for improved imaging in the subsequent screening step, e.g. a contrasting agent for improved imaging, which can be suitably selected and is not particularly limited. With regard to the choice of the subsequent screening step, again further data, e.g. further patient data, can be taken into account, e.g. whether a patient is allergic to a certain compound to be taken and/or whether a patient is not fit for a specific screening method.

According to certain embodiments, the subsequent screening step is carried out, and involves an analysis of the data obtained therein. A combination of these data with the data, e.g. the at least one image and/or first set of parameters, obtained in the first step allows a fast diagnosis of the patient with improved sensitivity and/or specificity, e.g. if the subsequent screening step is a liquid biopsy and/or a further medical imaging step with adapted parameters and/or preparation of the patient, e.g. by giving a contrasting agent to the patient. With the subsequent screening step it is possible that the results of the first step, i.e. the medical imaging in the first medical imaging apparatus, are further confirmed, thus leading to improved certainty for the diagnosis, or are revised, in which case the patient does not necessarily have to be confronted with the first positive result for cancer as the subsequent screening step can be carried out in sufficiently short time after the first medical imaging step.

According to certain embodiments, the first set of criteria comprises data for determining a specific sample, preferably a fluid sample, in the recommended subsequent screening step, wherein the recommended subsequent screening step comprises determining the specific sample, preferably the fluid sample. The criteria thus can provide a specific preselection of a sample to be taken, may it be blood, urine, saliva, a biopsy specimen, etc., based on the likelihood of a specific cancer and/or an easy and/or sufficiently specific method for deter mining a certain cancer. As stated before, also a multitude of cancers can be screened in a subsequent screening step, so that it is of course also not excluded that data for more than one specific sample are contained in the first set of criteria.

According to certain embodiments, the recommended subsequent screening step comprises obtaining or providing a sample, preferably a fluid sample, particularly the specific sample and preferably the flu id sample determined with the first set of criteria, of the patient; and carrying out an analysis of the sample, preferably flu id sample using the first set of criteria, optionally wherein the first set of criteria comprises a list comprising at least one reagent to be added to the sample, preferably the fluid sample.

The obtaining or providing of the sample is again not particularly restricted, but is preferably essentially non-invasive, further preferably non-invasive. It can again encompass taking a sample from the patient, which can be done by routine measures that can be carried out in the absence of a doctor, e.g. a standard method of taking a blood sample, taking a sample of urine, etc.

It is of course also not excluded in the obtaining or providing of a sample in the present method that the sample already has been taken before and is considered or reconsidered for analysis in a subsequent screening step.

In this regard the first set of criteria can then contain data that give instructions on how to analyze the sample. For example, it can contain information that specific genetic and/or epigenetic information is to be obtained in the sample, and can even contain data that suggest specific analysis steps and/or reagents to be used for analyzing the sample so that the analysis can be effectively carried out by routine measures. These can be of course adapted to the results in the first medical imaging step, so that the results thereof can be checked and possibly verified in a suitable manner.

According to certain embodiments, the subsequent screening step comprises or is a liquid biopsy, which is not particularly restricted. For example, when a CT-scanning has been carried out as a first medical imaging step, the subsequent screening step can be a liquid biopsy.

The liquid biopsy, also known as fluid biopsy, can be carried out on a suitable liquid sample of the patient, e.g. blood, urine, saliva, etc., and can be carried out in a routine manner, depending on the type of sample and the analysis to be carried out.

In this regard the first set of criteria can comprise a list for suitable steps to be carried out in the liquid biopsy, as well as factors to be considered, e.g. the type of sample to be taken, e.g. blood, urine, saliva, preferably blood, the type of target analyzed in the sample, e.g. circulating tumor cells, circulating DNA, changes assessed in the sample, e.g. concentration differences, mutations, epigenetic changes like DNA methylations, etc. In this regard the parameters for measuring and/or analyzing the sample can be adapted to the results obtained in the first medical imaging step, i.e. the first step. Also, the analysis method in liquid biopsy can be suitably determined in the first set of criteria, e.g. PCR, Next Generation Sequencing, mass spectrometry, etc.

For example, in the case of a CT imaging as first medical imaging step, a question in liquid biopsy could be if a tissue is actually malignant if only a small tissue part is considered to comprise cancer, whereas it could be assessed in liquid biopsy which treatment may be suitable if a bigger tissue part is observed that is likely malignant. Of course, also more than one analysis can be carried out in liquid biopsy, e.g. checking for tumor markers as well as for suitable treatment methods.

According to certain embodiments, the first set of criteria comprises a second set of parameters for carrying out a second medical imaging step in a second medical imaging apparatus, preferably wherein the recommended subsequent screening step further comprises an automated entry of the second set of parameters into the second medical imaging apparatus, optionally wherein the recommended subsequent screening step comprises obtaining a second medical image in the second medical imaging step. This second medical imaging step of course also can be carried out in addition to an analysis of a sample taken from the patient, e.g. in addition to a liquid biopsy.

The second set of parameters for carrying out the second medical imaging step in the second medical imaging apparatus is thereby not particularly restricted, and can contain e.g. settings for the medical imaging apparatus like irradiation dose, resolution, irradiation angles, precise locations of the image acquisition, etc. In this regard the second medical imaging apparatus can be also the first medical imaging apparatus, wherein the second medical imaging step is carried out with different parameters.

Thus, according to certain embodiments, the first set of criteria comprises a second set of parameters for carrying out a second medical imaging step in the first medical imaging apparatus, preferably wherein the recommended subsequent screening step further comprises an automated entry of the second set of parameters into the first medical imaging apparatus, optionally wherein the recommended subsequent screening step comprises obtaining a second medical image in the second medical imaging step.

Particularly, it is preferred that the second medical imaging step is carried out within a short time after the first medical imaging step if the first medical imaging apparatus is used for both steps. It is especially preferred that the patient at this time is still at the location where the first medical imaging step was carried out. For example, a low-dose CT scan as second medical imaging step could follow an ultralow-dose CT scan as first medical imaging step, wherein the patient may not be required to change the position, and wherein the decision for the second scan was made early enough for this subsequent imaging step to be carried out without the patient moving too much, e.g. within minutes, preferably within 10 minutes, further preferably within 5 minutes, even further preferably within 2 minutes, particularly preferably within 1 minute after the step of obtaining or providing the at least one first image of a tissue of the patient.

The automated entry of the second set of parameters into the first or second medical imaging apparatus for the recommended subsequent screening step is also not particularly restricted, and it can involve an automated setting of image acquisition parameters, etc. Also the obtaining a second medical image in the second medical imaging step is not particularly restricted and can—again—depend on the type of medical imaging apparatus, the cancer to be screened, etc.

According to certain embodiments, the method further comprising obtaining results from the recommended subsequent screening step, and preferably presenting the first set of parameters obtained in the first step and/or results obtained thereof as well as the results from the recommended subsequent screening step in a combined presentation. The type of presentation therein is not particularly restricted. It is not excluded that also the data of the first and subsequent screening steps are combined in a way for the practitioner, e.g. a doctor, to easily decide on a final diagnosis, e.g. by showing the probability of a cancer diagnosis in both steps next to each other.

Further, also an overall risk of cancer based on the individual results of the first and subsequent screening steps can be obtained.

According to certain embodiments, the results from the recommended subsequent screening step are used for a further analysis of the at least one first image. For example, results from a liquid biopsy as a subsequent screening steps can be used for a repeated analysis of the at least one first image of a tissue of the patient, e.g. with a focus on certain parameters, areas, etc. Also, if more than one tissue was scanned in the first step, e.g. during a full body scan, with a focus on one region, and multiple results indicating a cancer, e.g. multiple mutations and/or epigenetic changes, are obtained in a subsequent screening step, then the at least one first image can again be analyzed also for possible cancers in tissue other that the one that was the focus in the first step, and/or for metastases.

According to certain embodiments, the automated determination of a first set of parameters from the at least one first image and preferably an automated selection of a recommended subsequent screening step based on the first set of parameters is carried out using machine learning tools.

The machine learning tools therein are not particularly restricted and can include e.g. the use of neural networks, deep learning tools, etc.

According to certain embodiments, additionally a first set of patient data and/or a second set of general health-related data are additionally used in the automated determination whether a recommended subsequent screening step should be carried out based on the first set of parameters, and preferably used in an automated selection of a recommended subsequent screening step based on the first set of parameters. As already stated before, patient data therein can include general patient data, like age, sex, genetic information, pre-conditions, smoking behavior, alcohol and/or drug abuse, further medical conditions, allergies, etc. General health-related data can include country—and/or area-specific data, e.g. recommendations, as well as comparison data for patients of similar constitution, etc.

FIGS. 1 to 4 show schematically example step sequences in different embodiments of the method of the first aspect of the invention. FIG. 1 therein shows schematically an example method of the first aspect wherein in step 1 at least one first image of a tissue of the patient suspected of being carcinogenic using medical imaging in a first medical imaging apparatus is obtained or provided. In step 2 an automated determination of a first set of parameters from the at least one first image takes place, and in step 3 an automated determination whether a subsequent screening step should be carried out based on the first set of parameters. In step 4 a recommendation whether the subsequent screening step should be carried out is automatically displayed.

Figure 2:
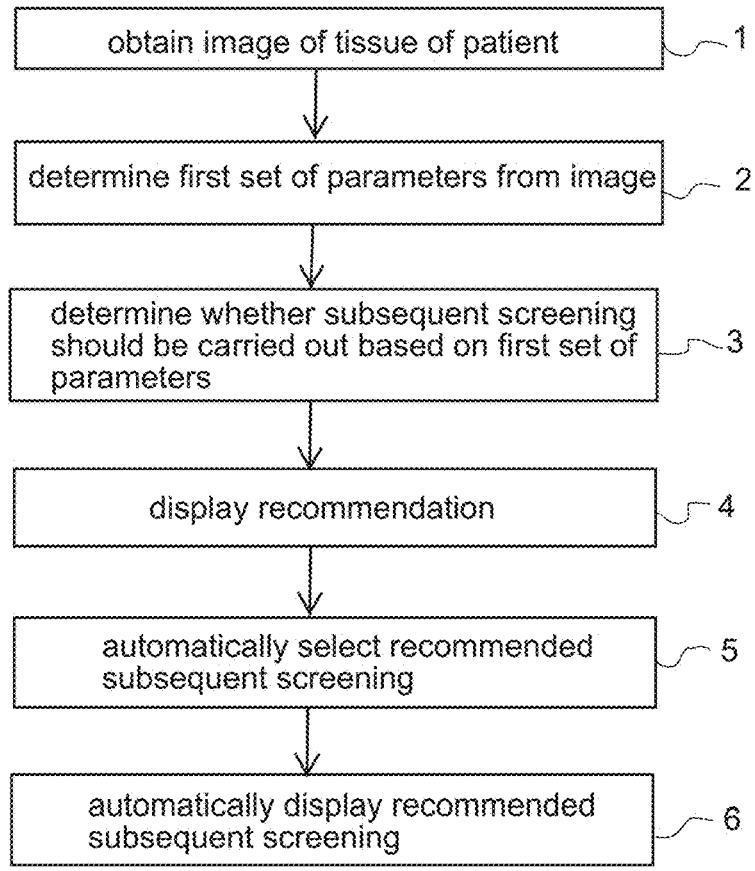

In the embodiment shown in FIG. 2 additionally a step 5 of an automated selection of a recommended subsequent screening step based on the first set of parameters, and a step 6 of an automated display of the recommended subsequent screening step are carried out after steps 1 to 4 as shown in the embodiment in FIG. 1.

Figure 3:
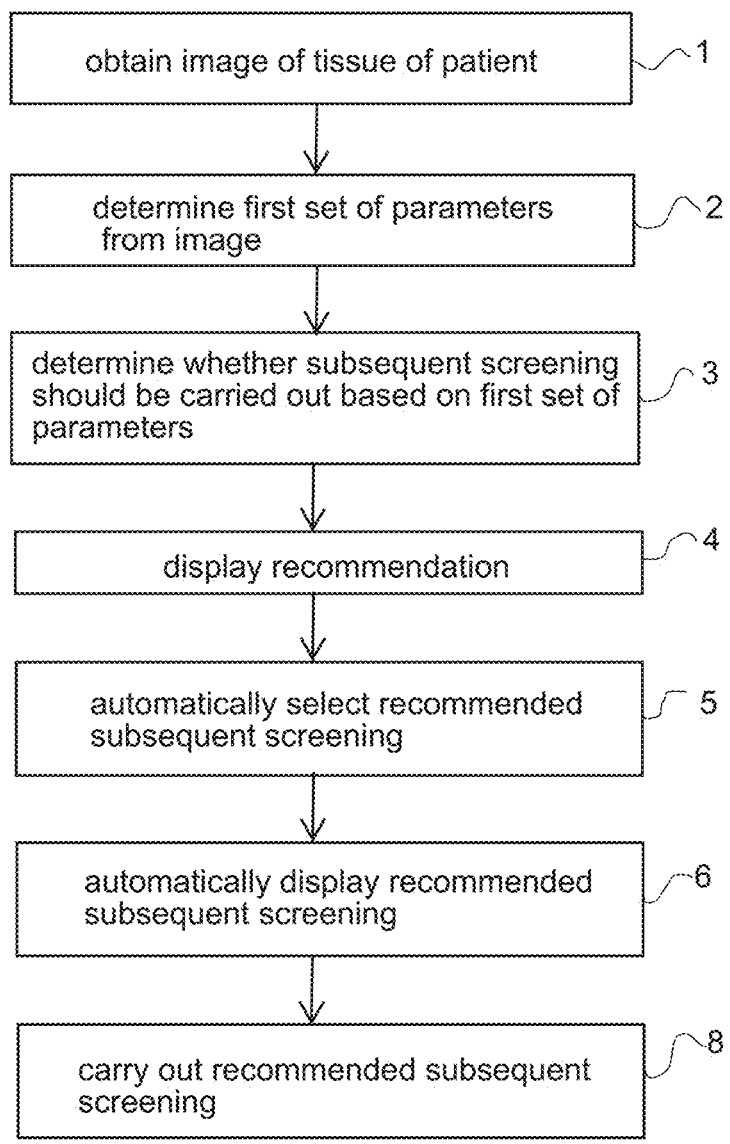

The embodiment of FIG. 3 corresponds to the one of FIG. 2, wherein after step 6 a step 8 of carrying out the recommended subsequent screening step occurs.

Figure 4:
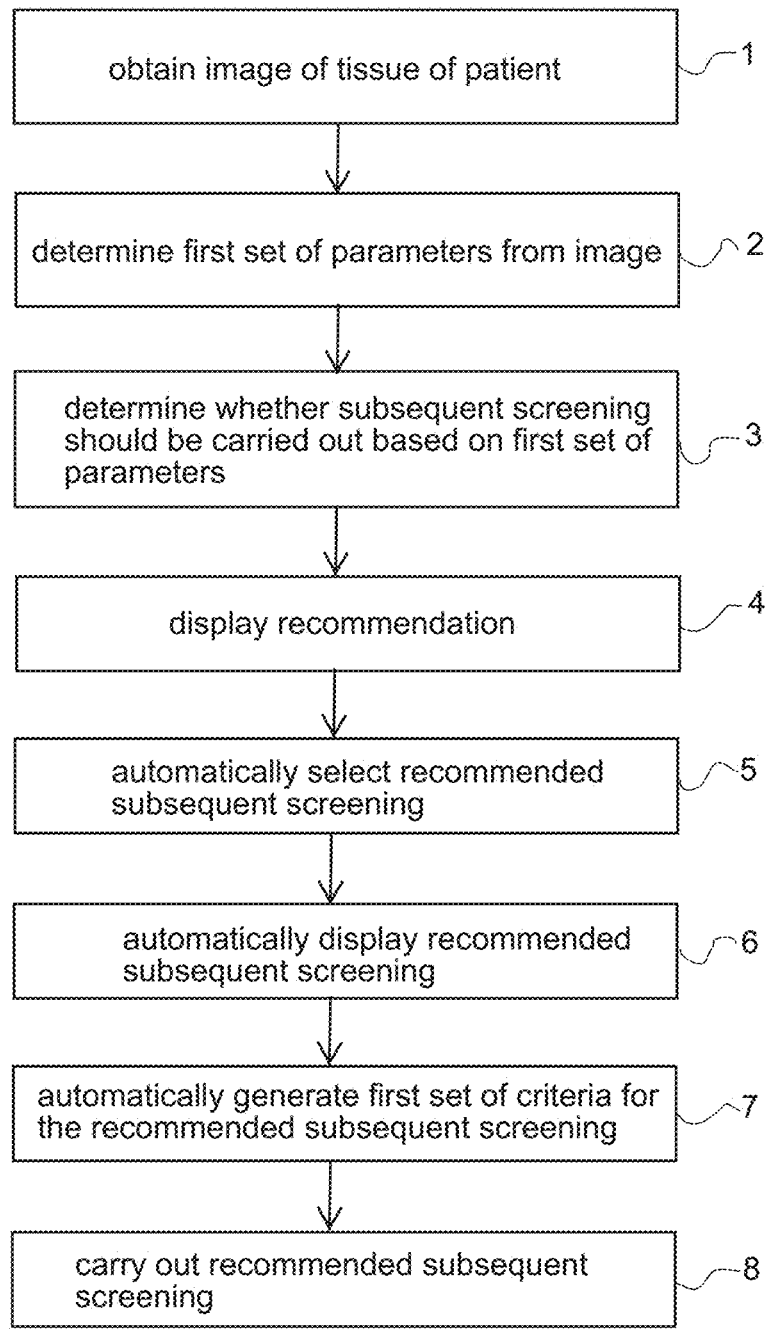

The embodiment shown schematically in FIG. 4 corresponds to the one in FIG. 3, wherein between steps 6 and 8 a step 7 of an automated generation of a first set of criteria for the recommended subsequent screening step using the first set of parameters is carried out, which then can be applied in step.

A second embodiment of the present invention relates to a method, particularly an integrated method, of screening for a cancer in a patient, comprising:

obtaining or providing in a first step at least one first image of a tissue of the patient suspected of being carcinogenic using medical imaging in a first medical imaging apparatus;

automated determination of a first set of parameters from the at least one first image;

automated selection of a recommended subsequent screening step based on the first set of parameters;

automated display of the recommended subsequent screening step; and optionally carrying out the recommended subsequent screening step.

In the method of the second aspect steps are applied that are already described with regard to the method of the first aspect, so that the description in regard to these steps also applies in this method of the second aspect. However, for completeness, the steps will be described in as much detail as needed again.

The method of the second embodiment particularly is an integrated method as it combines results from a first step in a first medical imaging apparatus, i.e. a first medical imaging step, with recommendations for a subsequent screening step that are generated from the results of the first medical imaging step.

According to certain embodiments, the steps in the method of the second aspect are carried out in the sequence given.

With this method particularly an early determination of a subsequent screening step with a follow-up diagnosis, as well as of parameters used in such a subsequent screening step, is possible, so that the subsequent screening step can be carried out while the patient is still present at the facility where at least one first image of a tissue of the patient suspected of being carcinogenic using medical imaging in a first medical imaging apparatus is obtained. This provides the person analyzing this information, e.g. a doctor, a tool for deciding what subsequent screening step is necessary for a diagnosis with sufficient sensitivity and/or specificity, without letting the patient wait for the final diagnosis. This way the number of early unclear diagnoses or even misdiagnoses can be reduced, while at the same time also a fast diagnosis from a subsequent screening step can be obtained, so that the patient will obtain a final diagnosis faster.

The obtaining or providing in a first step at least one first image of a tissue of the patient suspected of being carcinogenic using medical imaging in a first medical imaging apparatus is not particularly restricted. Particularly this step is non-invasive. In the present method also more than one image can be obtained in the first step, e.g. a multitude of images.

The medical imaging apparatus is therein not particularly restricted and those used for medical imaging can be applied, e.g. a computer tomography (CT) device, e.g. a computer tomography scanner, e.g. a low-dose computer tomograph, a magnetic resonance imaging (MRI) device like a magnetic resonance tomograph (MRT) device, a positron emission tomography (PET) device, e.g. a PET/CT or PET/MRT device, which can be used to scan a part of the body of a patient or used for a full body screening. The medical imaging apparatus as well as the method of obtaining or providing at least one first image with it can thereby be adapted to a specific diagnosis or expected diagnosis, e.g. for lung cancer screening with CT, breast cancer using MRI, etc. Also, it is not excluded that the first image is provided from a measurement that was intended for a different purpose, e.g. during trauma imaging, e.g. after an accident, etc.

According to certain embodiments, the at least one first image of a tissue of the patient suspected of being carcinogenic using medical imaging in a first medical imaging apparatus is obtained using a computed tomography scan and/or using magnetic resonance imaging, particularly low-dose computer tomography or even ultralow-dose computer tomography.

Again, the doses can depend e.g. on the tissue to be scanned, its location, etc. For example, a low-dose CT of the lung can be carried out with about 1 to 3 mSv, e.g. about 2 mSv, per scan, compared to the usual, normal about 6 mSv per scan in a normal CT. An ultralow-dose CT of the lung can even be carried out with about 0.5 mSv or less, particularly less than 0.5 mSv.

Particularly the present method is suitable for low-cost medical imaging methods with reduced sensitivity and/or specificity. For example, a CT measurement can be carried out as a first medical imaging step for e.g. a lung cancer, whereas a MRI based method can be used for e.g. breast cancer. Therefore, the present method can be e.g. directed to a screening for lung cancer, wherein in the first step a CT measurement device is used, and/or directed to a screening for breast cancer, wherein in the first step a MRI based measurement de vice is used.

Furthermore, the automated determination of a first set of parameters from the at least one first image is not particularly restricted, as long as it is carried out automatically. In this regard any suitable device can be used for the automated determination, e.g. suitable, e.g. computing device(s) that analyze the at least one first image, which can be integrated in the first medical imaging apparatus and/or can be located externally. Preferably, the device for analyzing the at least one image of a tissue of a patient, including an automated determination of a first set of parameters from the at least one first image, wherein also an automated determination whether a subsequent screening step should be carried out based on the first set of parameters is carried out, are located in the first medical imaging apparatus. The devices, particularly computing device(s), are not particularly restricted and can contain suitable algorithms for analyzing and evaluating the at least one first image of a tissue of the patient. According to certain embodiments, the devices can include machine learning tools, e.g. neural networks, deep learning, etc.

The analysis of the image in the automated determination of a first set of parameters is not particularly restricted. Several considerations can be taken into account for the analysis of the image, e.g. the location and/or size of tissue suspected of being carcinogenic, the shape of such a tissue, the texture of the tissue, the presence of further suspect tissue, e.g. metastases, the presence of features in the tissue like fringes, etc. For example, such parameters are readily known for studying lung cancer, where factors like roundness, the presence of fringes as example texture parameters, size, etc. are routinely considered.

Also, the automated determination of a first set of parameters can be carried out using additionally reference data, e.g. from other comparable images, e.g. the same body part, of other individuals, being recorded with the same first medical imaging apparatus and/or other medical imaging apparatuses delivering comparable results, e.g. of the same type.

The reference data can be from the patient that is screened, if available, and include data like age, smoking status, data on alcohol and/or drug abuse, height, weight, genetic risks, etc., as well as from other patients, like similar observations, similar risk group, etc., and they can be e.g. provided from a suitable database. Suitable determination methods for such a first set of parameters that can discriminate whether a cancer may be present in the patient based on the at least one first image can be chosen by the skilled person based on the type of image provided, the cancer that is screened for, etc., and may vary according to the tissue to be screened, the first medical imaging apparatus applied, etc. General statistical analysis methods like the determination of ROC (Receiver Operating Characteristic) curves, etc. can be carried out in the automated determination of a first set of parameters. According to certain embodiments, the automated determination of a first set of parameters from the at least one first image is carried out in or in the vicinity of the first medical imaging apparatus.

The first set of parameters is not particularly restricted and may depend on the type of cancer screened. It can involve any data that can be obtained from analysis of the at least one first image of a tissue of the patient, which is not particularly restricted. Examples thereof include location, size, shape, texture, etc. of a tissue suspected of being carcinogenic.

Furthermore, the automated selection of a recommended subsequent screening step based on the first set of parameters and/or the automated display of the recommended subsequent screening step are not particularly restricted.

Herein the automated selection of a recommended subsequent screening step based on the first set of parameters is not particularly restricted. While it is also possible that more than one subsequent screening step is recommended, according to certain embodiments only one subsequent screening step is recommended based on the first set of parameters. Particularly the subsequent screening step can also be suitably adapted to the patient, e.g. based on patient data.

The subsequent screening step is not particularly restricted, as long as it enables a further clarification of a cancer in a patient. At this stage it may also be possible to look for more than one cancer, e.g. if the first set of parameters gives a recommendation in this regard. Example subsequent screening steps will be given below, and can involve e.g. analyzing a sample from a patient that is to be obtained or has already been obtained before, e.g. in a liquid biopsy, e.g. a blood sample, and/or carrying out a second medical imaging step in a second medical imaging apparatus that can be the same as the first medical imaging apparatus or different.

The automated display of the recommended subsequent screening step can be together with the automated display of the at least one first image of a tissue of the patient and/or the first set of parameters automatically determined. However, the automated display of the recommended subsequent screening step can also be separate from either of these or all of these other displays.

The automated display of the recommended subsequent screening step preferably takes place within 15 minutes, preferably within 10 minutes, further preferably within 5 minutes, even further preferably within 2 minutes, particularly preferably within 1 minute after the step of obtaining or providing the at least one first image of a tissue of the patient. It is particularly preferably that the recommendation for the subsequent screening step is made available as fast as possible so that a practitioner, e.g. doctor, or another person with similar function can then decide whether this subsequent screening step is actually carried out, so that it can be carried out quickly after the obtaining of providing of the at least one first image, i.e. preferably while the patient that was screened is still present at a doctor's office and/or a hospital, so that the subsequent screening step can be carried out directly thereafter.

However, it is also possible that the automated display of the recommended subsequent screening step is not leading to the carrying out of the subsequent screening step shortly thereafter. It is also possible that the recommended subsequent screening step is actually a further monitoring of the tissue, e.g. again with the first medical imaging apparatus, after a sufficient time, e.g. a few days, weeks, or months, depending on the type of cancer suspected. If the subsequent screening step is carried out shortly after the recommendation of the subsequent screening step, it is preferred that it is carried out on the same day when or at least within a few days after the least one first image of a tissue of the patient suspected of being carcinogenic using medical imaging in a first medical imaging apparatus is obtained or provided. At least parts thereof, e.g. the taking of a sample and/or the taking of at least one second image in a second medical imaging apparatus—which can be the same or different as the first medical imaging apparatus—is then preferably carried out within 4 hours, preferably less than 3 hours, preferably within 2 hours, further preferably within 1 our, further preferably within less than 1 hour, more preferably within 30 minutes, after the at least one first image of a tissue of the patient suspected of being carcinogenic using medical imaging in a first medical imaging apparatus is obtained or provided.

According to certain embodiments, the recommended subsequent screening step is carried out within 4 hours, preferably less than 3 hours, preferably within 2 hours, further preferably within 1 hour, further preferably within less than 1 hour, more preferably within 30 minutes, after the first step.

Particularly this is useful if further interaction is required from the patient, e.g. by obtaining or providing a sample, preferably a liquid sample, e.g. a blood sample, and/or if a further screening using a second medical imaging apparatus, which can be the same as the first imaging apparatus or be different, is carried out, wherein it is even possible that the patient may have to take a compound like a contrasting agent for improved imaging.

The optional carrying out the recommended subsequent screening step is not particularly restricted, but is preferably essentially non-invasive, further preferably non-invasive. It can encompass taking a sample from the patient, though, which can be done by routine measures that can be carried out in the absence of a doctor, e.g. a standard method of taking a blood sample, taking a sample of urine, etc., and/or encompass the patient taking one or more compounds for improved imaging in the subsequent screening step, e.g. a contrasting agent for improved imaging, which can be suitably selected and is not particularly limited. With regard to the choice of the subsequent screening step, also further data, e.g. further patient data, can be taken into account, e.g. whether a patient is allergic to a certain compound to be taken and/or whether a patient is not fit for a specific screening method.

According to certain embodiment, the method further comprises an automated generation of a first set of criteria for the recommended subsequent screening step using the first set of parameters; and optionally carrying out the recommended subsequent screening step using the first set of criteria.

The automated generation of a first set of criteria for the recommended subsequent screening step using the first set of parameters is not particularly limited, and again can involve using suitable computing means, e.g. including machine learning tools, as well as using further data, e.g. patient data and/or further reference data. The first set of criteria can then again be automatically displayed and/or automatically applied in the subsequent screening step, and can involve data like analyzing steps and/or agents to be used on a sample of the patient, and/or settings for a subsequent, second medical imaging step.

In this regard also the subsequent screening step, e.g. a liquid biopsy and/or a further, second medical imaging step, and/or the first set of criteria can be adapted with regard to the sensitivity and/or specificity that is to be obtained, also in view of the results obtained in the first medical imaging step. Furthermore, the optional carrying out the recommended subsequent screening step using the first set of criteria is not particularly restricted, but is preferably essentially non-invasive, further preferably non-invasive. It can again encompass taking a sample from the patient, which can be done by routine measures that can be carried out in the absence of a doctor, e.g. a standard method of taking a blood sample, taking a sample of urine, etc., and/or encompass the patient taking one or more compounds for improved imaging in the subsequent screening step, e.g. a contrasting agent for improved imaging, which can be suitably selected and is not particularly limited. With regard to the choice of the subsequent screening step, again further data, e.g. further patient data, can be taken into account, e.g. whether a patient is allergic to a certain compound to be taken and/or whether a patient is not fit for a specific screening method.

According to certain embodiments, the subsequent screening step is carried out, and involves an analysis of the data obtained therein. A combination of these data with the data, e.g. the at least one image and/or first set of parameters, obtained in the first step allows a fast diagnosis of the patient with improved sensitivity and/or specificity, e.g. if the subsequent screening step is a liquid biopsy and/or a further medical imaging step with adapted parameters and/or preparation of the patient, e.g. by giving a contrasting agent to the patient. With the subsequent screening step it is possible that the results of the first step, i.e. the medical imaging in the first medical imaging apparatus, are further confirmed, thus leading to improved certainty for the diagnosis, or are revised, in which case the patient does not necessarily have to be confronted with the first positive result for cancer as the subsequent screening step can be carried out in sufficiently short time after the first medical imaging step.

According to certain embodiments, the first set of criteria comprises data for determining a specific sample, preferably a fluid sample, in the recommended subsequent screening step, wherein the recommended subsequent screening step comprises determining the specific sample, preferably the fluid sample. The criteria thus can provide a specific preselection of a sample to be taken, may it be blood, urine, saliva, a biopsy specimen, etc., based on the likelihood of a specific cancer and/or an easy and/or sufficiently specific method for deter mining a certain cancer. As stated before, also a multitude of cancers can be screened in a subsequent screening step, so that it is of course also not excluded that data for more than one specific sample are contained in the first set of criteria.

According to certain embodiments, the recommended subsequent screening step comprises obtaining or providing a sample, preferably a fluid sample, particularly the specific sample and preferably the flu id sample determined with the first set of criteria, of the patient; and carrying out an analysis of the sample, preferably flu id sample using the first set of criteria, optionally wherein the first set of criteria comprises a list comprising at least one reagent to be added to the sample, preferably the fluid sample.

The obtaining or providing of the sample is again not particularly restricted, but is preferably essentially non-invasive, further preferably non-invasive. It can again encompass taking a sample from the patient, which can be done by routine measures that can be carried out in the absence of a doctor, e.g. a standard method of taking a blood sample, taking a sample of urine, etc.

It is of course also not excluded in the obtaining or providing of a sample in the present method that the sample already has been taken before and is considered or reconsidered for analysis in a subsequent screening step.

In this regard the first set of criteria can then contain data that give instructions on how to analyze the sample. For example, it can contain information that specific genetic and/or epigenetic information is to be obtained in the sample, and can even contain data that suggest specific analysis steps and/or reagents to be used for analyzing the sample so that the analysis can be effectively carried out by routine measures. These can be of course adapted to the results in the first medical imaging step, so that the results thereof can be checked and possibly verified in a suitable manner.

According to certain embodiments, the subsequent screening step comprises or is a liquid biopsy, which is not particularly restricted. For example, when a CT-scanning has been carried out as a first medical imaging step, the subsequent screening step can be a liquid biopsy.

The liquid biopsy, also known as fluid biopsy, can be carried out on a suitable liquid sample of the patient, e.g.

blood, urine, saliva, etc., and can be carried out in a routine manner, depending on the type of sample and the analysis to be carried out.

In this regard the first set of criteria can comprise a list for suitable steps to be carried out in the liquid biopsy, as well as factors to be considered, e.g. the type of sample to be taken, e.g. blood, urine, saliva, preferably blood, the type of target analyzed in the sample, e.g. circulating tumor cells, circulating DNA, changes assessed in the sample, e.g. concentration differences, mutations, epigenetic changes like DNA methylations, etc. In this regard the parameters for measuring and/or analyzing the sample can be adapted to the results obtained in the first medical imaging step, i.e. the first step. Also, the analysis method in liquid biopsy can be suitably determined in the first set of criteria, e.g. PCR, Next Generation Sequencing, mass spectrometry, etc.

For example, in the case of a CT imaging as first medical imaging step, a question in liquid biopsy could be if a tissue is actually malignant if only a small tissue part is considered to comprise cancer, whereas it could be assessed in liquid biopsy which treatment may be suitable if a bigger tissue part is observed that is likely malignant. Of course, also more than one analysis can be carried out in liquid biopsy, e.g. checking for tumor markers as well as for suitable treatment methods.

According to certain embodiments, the first set of criteria comprises a second set of parameters for carrying out a second medical imaging step in a second medical imaging apparatus, preferably wherein the recommended subsequent screening step further comprises an automated entry of the second set of parameters into the second medical imaging apparatus, optionally wherein the recommended subsequent screening step comprises obtaining a second medical image in the second medical imaging step.

This second medical imaging step of course also can be carried out in addition to an analysis of a sample taken from the patient, e.g. in addition to a liquid biopsy.

The second set of parameters for carrying out the second medical imaging step in the second medical imaging apparatus is thereby not particularly restricted, and can contain e.g. settings for the medical imaging apparatus like irradiation dose, resolution, irradiation angles, precise locations of the image acquisition, etc. In this regard the second medical imaging apparatus can be also the first medical imaging apparatus, wherein the second medical imaging step is carried out with different parameters. Thus, according to certain embodiments, the first set of criteria comprises a second set of parameters for carrying out a second medical imaging step in the first medical imaging apparatus, preferably wherein the recommended subsequent screening step further comprises an automated entry of the second set of parameters into the first medical imaging apparatus, optionally wherein the recommended subsequent screening step comprises obtaining a second medical image in the second medical imaging step.

Particularly, it is preferred that the second medical imaging step is carried out within a short time after the first medical imaging step if the first medical imaging apparatus is used for both steps. It is especially preferred that the patient at this time is still at the location where the first medical imaging step was carried out. For example, a low-dose CT scan as second medical imaging step could follow an ultralow-dose CT scan as first medical imaging step, wherein the patient may not be required to change the position, and wherein the decision for the second scan was made early enough for this subsequent imaging step to be carried out without the patient moving too much, e.g. within 15 minutes, preferably within 10 minutes, further preferably within 5 minutes, even further preferably within 2 minutes, particularly preferably within 1 minute after the step of obtaining or providing the at least one first image of a tissue of the patient.

The automated entry of the second set of parameters into the first or second medical imaging apparatus for the recommended subsequent screening step is also not particularly restricted, and it can involve an automated setting of image acquisition parameters, etc. Also the obtaining a second medical image in the second medical imaging step is not particularly restricted and can—again—depend on the type of medical imaging apparatus, the cancer to be screened, etc. According to certain embodiments, the method further comprising obtaining results from the recommended subsequent screening step, and preferably presenting the first set of parameters obtained in the first step and/or results obtained thereof as well as the results from the recommended subsequent screening step in a combined presentation. The type of presentation therein is not particularly restricted. It is not excluded that also the data of the first and subsequent screening steps are combined in a way for the practitioner, e.g. a doctor, to easily decide on a final diagnosis, e.g. by showing the probability of a cancer diagnosis in both steps next to each other.

Further, also an overall risk of cancer based on the individual results of the first and subsequent screening steps can be obtained.

According to certain embodiments, the results from the recommended subsequent screening step are used for a further analysis of the at least one first image. For example, results from a liquid biopsy as a subsequent screening steps can be used for a repeated analysis of the at least one first image of a tissue of the patient, e.g. with a focus on certain parameters, areas, etc. Also, if more than one tissue was scanned in the first step, e.g. during a full body scan, with a focus on one region, and multiple results indicating a cancer, e.g. multiple mutations and/or epigenetic changes, are obtained in a subsequent screening step, then the at least one first image can again be analyzed also for possible cancers in tissue other that the one that was the focus in the first step, and/or for metastases.

According to certain embodiments, the automated determination of a first set of parameters from the at least one first image and preferably an automated selection of a recommended subsequent screening step based on the first set of parameters is carried out using machine learning tools. The machine learning tools therein are not particularly restricted and can include e.g. the use of neural networks, deep learning tools, etc.

According to certain embodiments, additionally a first set of patient data and/or a second set of general health-related data are additionally used in the automated determination whether a recommended subsequent screening step should be carried out based on the first set of parameters, and prefer ably used in an automated selection of a recommended subsequent screening step based on the first set of parameters. As already stated before, patient data therein can include general patient data, like age, sex, genetic information, pre-conditions, smoking behavior, alcohol and/or drug abuse, further medical conditions, allergies, etc. General health-related data can include country—and/or area-specific data, e.g. recommendations, as well as comparison data for patients of similar constitution, etc.

Figure 5:
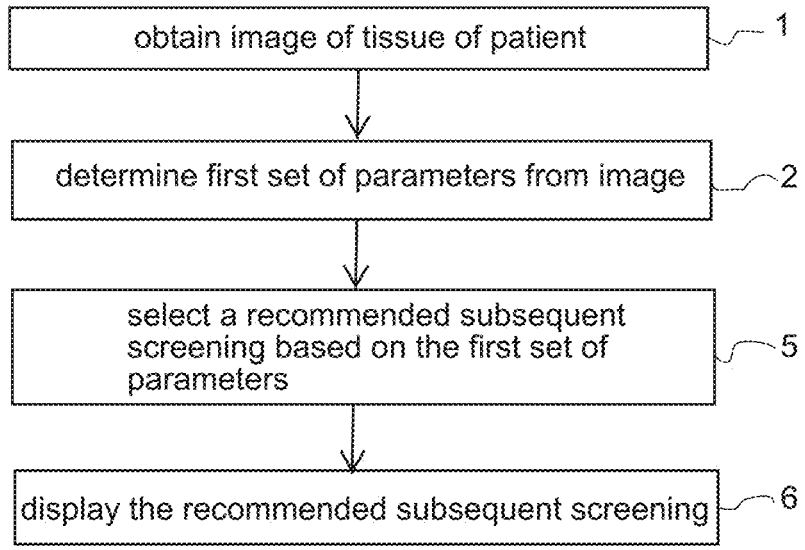
FIGS. 5 to 7 show schematically steps in a method of the second embodiment of the invention.
Figure 6:
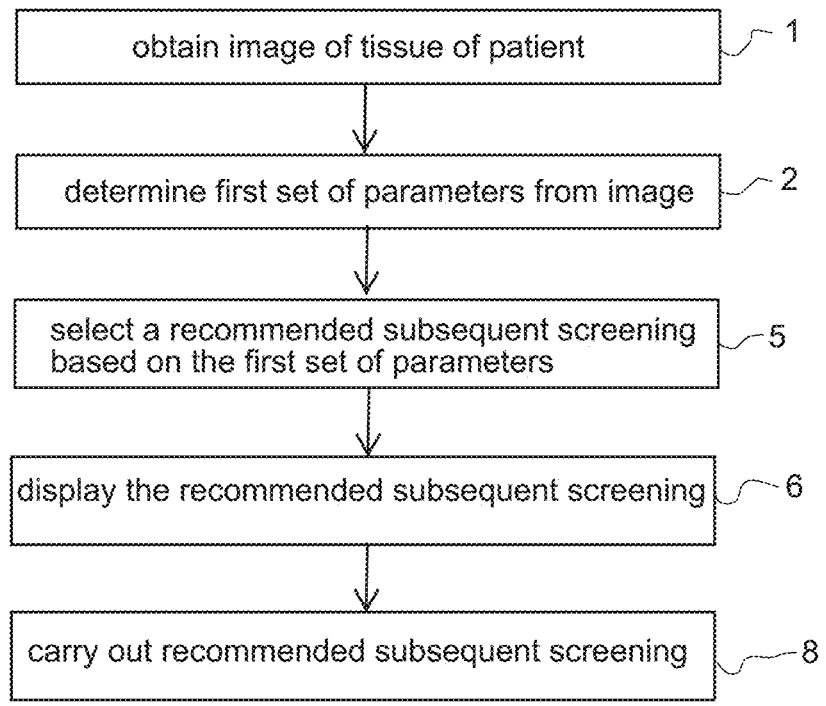
Figure 7:
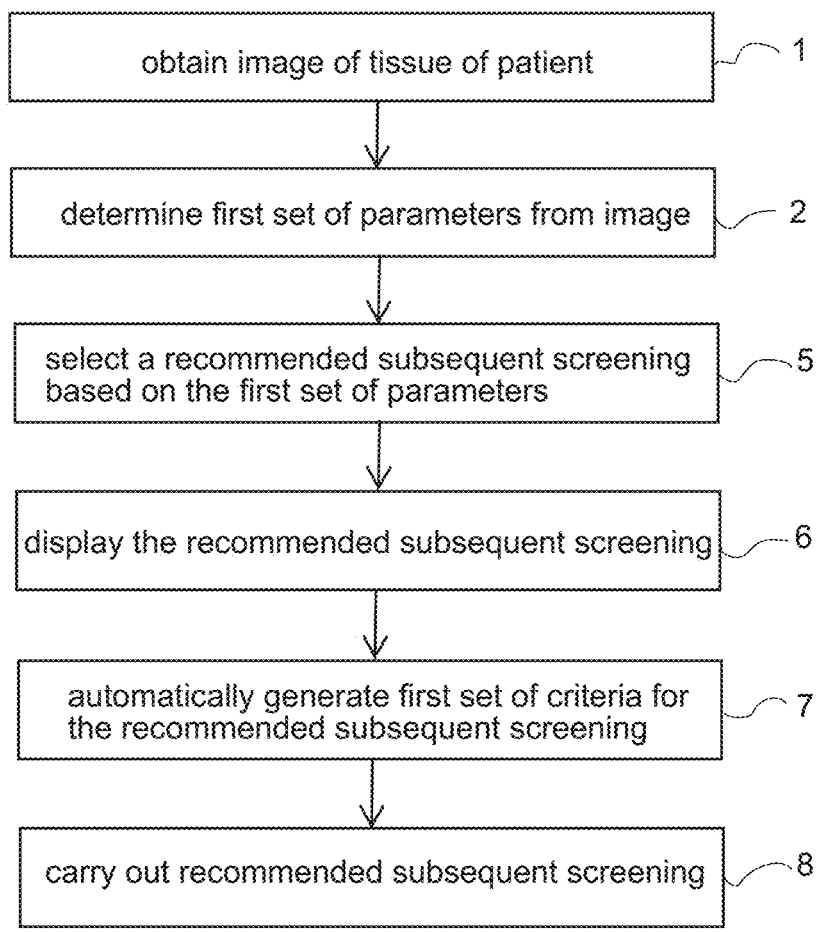

FIGS. 5 to 7 show schematically example step sequences in different embodiments of the method of the second embodiment of the invention.

FIG. 5 therein shows schematically an example method of the second embodiment wherein in step 1 at least one first image of a tissue of the patient suspected of being carcinogenic using medical imaging in a first medical imaging apparatus is obtained or provided. In step 2 an automated determination of a first set of parameters from the at least one first image takes place. Additionally a step 5 of an automated selection of a recommended subsequent screening step based on the first set of parameters, and a step 6 of an automated display of the recommended subsequent screening step are carried out thereafter. The embodiment of FIG. 6 corresponds to the one of FIG. 5, wherein after step 6 a step 8 of carrying out the recommended subsequent screening step occurs.

The embodiment shown schematically in FIG. 7 corresponds to the one in FIG. 6, wherein between steps 6 and 8 a step 7 of an automated generation of a first set of criteria for the recommended subsequent screening step using the first set of parameters is carried out, which then can be applied in step.

Also disclosed is a computer program product comprising computer executable instructions which, when executed, perform a method according to the first and/or second embodiment.

In certain embodiments the computer program product is one on which program commands or program codes of a computer program for executing the method are stored. According to certain embodiments the computer program product is a storage medium. According to certain embodiments, it is stored in a medical imaging apparatus and connected to further hardware in the medical imaging apparatus, e.g. input and output screens, as well as hardware for setting measurement parameters in the medical imaging apparatus.

The computer program product therein can include machine learning tools.

An embodiment of the present invention also relates to the use of the computer program product in a method of the first and/or second method of embodiments of the invention.

Furthermore, a medical imaging apparatus of the fourth embodiment is disclosed, comprising:

means for obtaining at least one first image of a tissue of a patient; and means for analyzing the at least one image of a tissue of a patient, including an automated determination of a first set of parameters from the at least one first image, wherein also an automated determination whether a subsequent screening step should be carried out based on the first set of parameters is carried out; and means for displaying results of the analyzation of the at least one image of a tissue of a patient; and means for displaying the result of the automated determination whether a subsequent screening step should be carried out based on the first set of parameters.

With the medical imaging apparatus of an embodiment of the invention, the method of the first and/or second embodiment of the invention, particularly the first aspect, can be carried out. Therefore the descriptions particularly with regard to the method of the first aspect also apply to the medical imaging apparatus of the fourth embodiment.

The device(s) for obtaining at least one first image of a tissue of a patient are not particularly restricted, but are preferably non-invasive. They can e.g. comprise a computer tomograph and/or a MRI (magnetic resonance imaging) scanner.

Also the device(s) for analyzing the at least one image of a tissue of a patient, including an automated determination of a first set of parameters from the at least one first image, wherein also an automated determination whether a subsequent screening step should be carried out based on the first set of parameters is carried out, are not particularly limited. They can include the computer program product of the present invention. Further, the means for displaying results of the analyzation of the at least one image of a tissue of a patient are not particularly restricted, and can include e.g. a screen, a display, a handheld device like a tablet, etc.

In addition, the device(s) for displaying the result of the automated determination whether a subsequent screening step should be carried out based on the first set of parameters is not particularly restricted. It can include any form of display, or parts of a display, e.g. a part of the means for displaying results of the analyzation of the at least one image of a tissue of a patient. For example, it can include an extra field on the means for displaying results of the analyzation of the at least one image of a tissue of a patient wherein the field can indicate the recommendation whether a subsequent screening step should be carried out based on the first set of parameters. Such a field or display is not particularly restricted and can be in the form of e.g. a button with changing colors that may also start blinking, a text field giving out more detailed recommendations, a signaling unit which gives an audible signal as an indication that a subsequent screening step should be carried out, a mixture thereof, etc. However, as the patient should normally still present when the means for displaying the result of the automated determination whether a subsequent screening step should be carried out based on the first set of parameters actually display whether a subsequent screening step should be carried out, a non-audible display is preferred to not alarm the patient.

Furthermore the medical imaging apparatus can include device(s) for displaying recommendations for a subsequent step, which are also not particularly restricted. It can include any form of display, or parts of a display, e.g. a part of the means for displaying results of the analyzation of the at least one image of a tissue of a patient and/or the means for displaying the result of the automated determination whether a subsequent screening step should be carried out based on the first set of parameters. For example, it can include an extra field on the means for displaying results of the analyzation of the at least one image of a tissue of a patient. Such a field or display is not particularly restricted and can be in the form of a text field giving out more detailed recommendations, etc.

In the medical imaging apparatus, the device(s) for displaying results of the analyzation of the at least one image of a tissue of a patient, the means for displaying the result of the automated determination whether a subsequent screening step should be carried out based on the first set of parameters, and/or optionally the means for displaying recommendations for a subsequent step can be combined in a first display unit, which is not particularly restricted, and can be a handheld device connected to the medical imaging apparatus—also e.g. wirelessly, a screen, a display, etc.

Apart from the above features, the present medical imaging apparatus can also include components that are usually present in medical imaging apparatuses.

Figure 8:
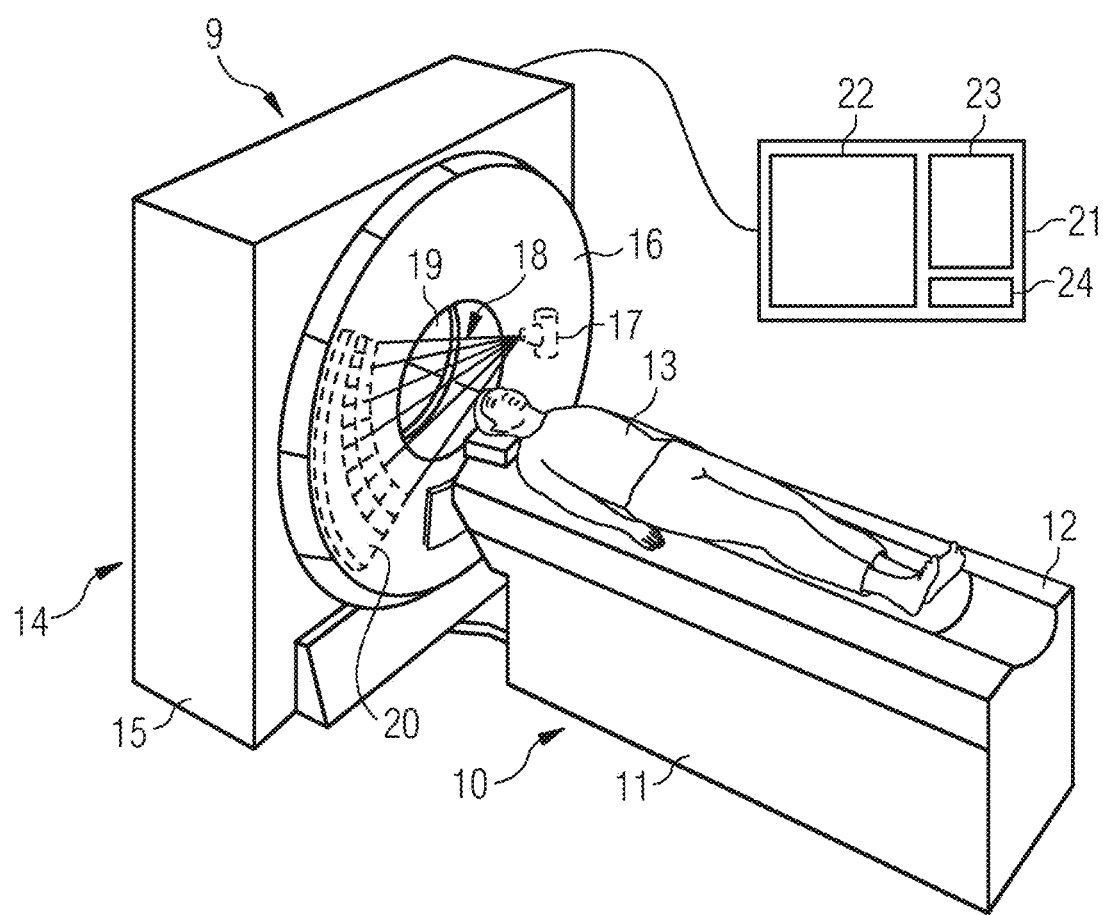
In FIG. 8 an example of a medical imaging apparatus of an embodiment of the present invention is depicted schematically.

An example medical imaging apparatus 9 is schematically shown in FIG. 8 in the form of a CT device. In FIG. 8 a gantry is shown, and a fixture 10 for the patient 13 to lie on, including a fixture table 11 and a movable transfer plate 12.

The gantry 14 includes a tunnel-like opening 19 through which the movable transfer plate 12 can be moved, a stationary support frame 15, a rotor 16, a radiation source 17, particularly for X-rays, from which radiation 18, e.g. X-rays, is emit ted, and a detector 20.

With the medical imaging apparatus 9 image acquisition can be carried out in a usual way, as well as image analysis.

The results of the analysis can be shown in first display unit 21, e.g. in the form of a handheld device (not to scale), which comprises device 22 for displaying results of the analyzation of at least one image of a tissue of a patient recorded with the gantry 14, device 24 for displaying result of an automated determination whether a subsequent screening step should be carried out based on the first set of parameters obtained from analyzing the at least one image of a tissue of the patient, and optionally device 23 for displaying recommendations for a subsequent step based on the first set of parameters.

In addition, a medical imaging apparatus of the fifth embodiment is disclosed, comprising:

device(s) for obtaining at least one first image of a tissue of a patient; and device(s) for analyzing the at least one image of a tissue of a patient, including an automated determination of a first set of parameters from the at least one first image, wherein also an automated determination whether a subsequent screening step should be carried out based on the first set of parameters is carried out; and device(s) for displaying results of the analyzation of the at least one image of a tissue of a patient;

further comprising:

device(s) for displaying recommendations for a subsequent screening step based on the first set of parameters.

With the medical imaging apparatus of the invention, the method of the first and/or second embodiment of the invention, particularly the second embodiment, can be carried out. Therefore the descriptions particularly with regard to the method of the second embodiment also apply to the medical imaging apparatus of the fifth embodiment.

The device(s) for obtaining at least one first image of a tissue of a patient are not particularly restricted, but are prefer ably non-invasive. They can e.g. comprise a computer tomograph and/or a MRI (magnetic resonance imaging) scanner.

Also the device(s) for analyzing the at least one image of a tissue of a patient, including an automated determination of a first set of parameters from the at least one first image, wherein also an automated determination whether a subsequent screening step should be carried out based on the first set of parameters is carried out, are not particularly limited. They can include the computer program product of embodiments of the present invention.

Further, the device(s) for displaying results of the analyzation of the at least one image of a tissue of a patient are not particularly restricted, and can include e.g. a screen, a display, a handheld device like a tablet, etc. Furthermore the medical imaging apparatus includes device(s) for displaying recommendations for a subsequent screening step, which are also not particularly restricted. It can include any form of display, or parts of a display, e.g. a part of the means for displaying results of the analyzation of the at least one image of a tissue of a patient. For example, it can include an extra field on the means for displaying results of the analyzation of the at least one image of a tissue of a patient. Such a field or display is not particularly restricted and can be in the form of a text field giving out more detailed recommendations, etc.

In the medical imaging apparatus, the device(s) for displaying results of the analyzation of the at least one image of a tissue of a patient and the means for displaying recommendations for a subsequent step can be combined in a first display unit, which is not particularly restricted, and can be a handheld device connected to the medical imaging apparatus—also e.g. wirelessly, a screen, a display, etc.

Apart from the above features, the present medical imaging apparatus can also include components that are usually present in medical imaging apparatuses.

The above embodiments can be combined arbitrarily, if appropriate. Further possible embodiments and implementations of embodiments of the invention comprise also combinations of features not explicitly mentioned in the foregoing or in the following with regard to the Examples of embodiments of the invention. Particularly, a person skilled in the art will also add individual aspects as improvements or additions to the respective basic form of embodiments of the invention.

EXAMPLES

Embodiments of the present invention will now be described in detail with reference to several examples thereof. However, these examples are illustrative and do not limit the scope of the invention.

Implementation Example: Lung Cancer Screening

In a first example step of a method of an embodiment of the present invention a very low-dose screening CT is performed and is analyzed in real time by a CAD (Computer Aided Diagnosis; Computer Aided Detection) algorithm; to perform this in real time, it may be necessary to run the CAD algorithm directly on a processor integrated in the CT scanner to avoid time consuming transfer of large data sets through the hospital network, but this of course does not restrict this first step. If the CAD algorithm detects a suspicious lesion, follow-up steps may be triggered immediately, while the patient is still in the diagnostic unit, or even on the patient table of the CT scanner. These immediate follow up steps may include a second CT scan with full diagnostic quality (at increased dose) and/or drawing of a blood sample, e.g. for a liquid biopsy, for example by searching for tumor specific mutations in circulating cell free DNA and enabling molecular profiling of a potential tumor.

These follow up steps after the CAD analysis of the initial low-dose CT may be performed fully automatically or—as it may be legally required—the system suggests these steps to the physician and the physician decides and releases these next steps, so that the method represents a type of Clinical Decision Support System.

Also, there may be an additional step included to perform a POC (point of care) lab test to find out if the patient will tolerate contrast agent and then perform the diagnostic CT with contrast agent. The decision on performing a comprehensive molecular profiling on the blood sample that was collected during that initial session may be triggered based on the radiological results of the diagnostic CT to avoid unnecessary cost.

The following advantages are obtained. If the screening CT is negative, the patient is only exposed to the minimal dose and there are no costs for any additional steps. The result of the CAD algorithm may be verified by a radiologist offline in the next days. If on the other hand the screening CT shows a suspicious lesion, next steps can automatically be triggered before the patient leaves the institution. This avoids de lays, cost and non-compliance issues that would arise if the patient leaves and has to be contacted to schedule a new appointment. The physician rather would have access to all relevant diagnostic data after the first session, including for example screening CT, diagnostic CT, molecular profiling etc. and could decide on therapy options without delay based on comprehensive data.

For healthy persons cost and side effects are not increased using the present method compared to the conventional approach. For cancer patients diagnosis can be performed with maximum speed and accuracy and in a personalized way. This may improve patient's outcomes due to faster start of precision treatment.

By applying the present methods, the accuracy of screening programs may be improved. The sensitivity can be optimized, e.g. by parameters of the CAD algorithm to avoid missing small lesions. The specificity can be improved, e.g. by including additional information from imaging and molecular di agnostics directly into the initial screening session, rather than communication a false positive finding that would lead to patient anxiety, avoidable cost and side effects. The automated determination of a first set of parameters from the first medical imaging step, e.g. using an automatic algorithm, is not intended to replace the physician, but to help to improve and speed up decisions about next diagnostic and therapeutic steps, comparable to Appropriate Use Criteria.

Embodiments of the present invention enables an automatic and individualized implementation of a variety of diagnostic steps covering different modalities in dependence of the result of preceding screening and diagnostic steps.

The invention claimed is:

1. A method of screening for a cancer in a patient, the method comprising:
   obtaining or providing at least one first image of a tissue of said patient using medical imaging via a first medical imaging apparatus, the tissue suspected of being carcinogenic;
   automatically determining a first set of parameters from said at least one first image;
   automatically determining whether subsequent screening should be carried out based on the first set of parameters;
   automatically selecting a recommended subsequent screening based on the first set of parameters;
   automatically generating a first set of criteria for the recommended subsequent screening using the first set of parameters, the first set of criteria including at least one reagent to be added to a sample of the patient; and
   automatically displaying, via a first display unit, the recommended subsequent screening;
   wherein the automatically displaying of the recommended subsequent screening takes place within 15 minutes after the obtaining or providing of the at least one first image of the tissue of the patient.

2. The method of claim 1, wherein the first set of criteria comprises data for determining a specific sample in the recommended subsequent screening, and wherein the recommended subsequent screening comprises determining the specific sample.

3. The method of claim 2, wherein the specific sample is a fluid sample, and wherein the recommended subsequent screening comprises determining the fluid sample.

4. The method of claim 1, wherein the recommended subsequent screening comprises:
   obtaining or providing the sample; and
   analyzing the sample, using the first set of criteria.

5. The method of claim 4, wherein the first set of criteria comprises a second set of parameters for carrying out a second medical imaging in a second medical imaging apparatus, wherein the recommended subsequent screening comprises an automated entry of the second set of parameters into the second medical imaging apparatus, and wherein the recommended subsequent screening comprises obtaining a second medical image in the second medical imaging.

6. The method of claim 1, wherein the first set of criteria comprises a second set of parameters for carrying out a second medical imaging in a second medical imaging apparatus, wherein the recommended subsequent screening comprises an automated entry of the second set of parameters into the second medical imaging apparatus, and wherein the recommended subsequent screening comprises obtaining a second medical image in the second medical imaging.

7. The method of claim 1, further comprising:
   obtaining results from the recommended subsequent screening, and at least one of presenting the first set of parameters and the results or presenting the results from the recommended subsequent screening in a combined presentation.

8. The method of claim 7, further comprising:
   analyzing the at least one first image based on the results from the recommended subsequent screening.

9. The method of claim 1, wherein the obtaining or providing the at least one first image includes using at least one of a computed tomography scan or magnetic resonance imaging.

10. The method of claim 1, wherein the recommended subsequent screening is carried out less than 3 hours, after the obtaining the at least one first image.

11. The method of claim 1, wherein the automatically determining the first set of parameters is carried out using machine learning tools.

12. The method of claim 1, wherein the automatically determining whether subsequent screening should be carried out is further based on at least one of a first set of patient data or a second set of general health-related data.

13. The method of claim 1, further comprising:
   carrying out the recommended subsequent screening.

14. The method of claim 1 further comprising:
   carrying out the recommended subsequent screening using the first set of criteria.

15. The method of claim 1, wherein the first set of criteria includes a list of suitable steps to be carried out in the subsequent screening and as factors to be considered for the recommended subsequent screening, the list including at least one of
   a type of a sample to be taken,
   a type of target analyzed in the sample, or
   changes assessed in the sample.

16. An integrated method of screening for a cancer in a patient, the method comprising:
   obtaining or providing at least one first image of a tissue of said patient using medical imaging via a first medical imaging apparatus, the tissue suspected of being carcinogenic;
   automatically determining a first set of parameters from said at least one first image;
   automatically determining whether a subsequent screening should be carried out based on the first set of parameters;
   automatically determining a plurality of subsequent screenings based on the first set of parameters, in response to determining that a subsequent screening should be carried out;

automatically selecting a recommended subsequent screening from among the plurality of subsequent screenings;

automatically generating a first set of criteria for the recommended subsequent screening using the first set of parameters, the first set of criteria including at least one reagent to be added to a sample of the patient; and automatically displaying the recommended subsequent screening.

17. A non-transitory computer program product, storing computer executable instructions which, when executed, perform the method of claim 1.

18. A medical imaging apparatus, comprising:
a processor configured to cause the medical imaging apparatus to
obtain at least one first image of a tissue of a patient,
determine a first set of parameters from said at least one first image,
determine whether a subsequent screening should be carried out based on the first set of parameters,
determine a plurality of subsequent screenings based on the first set of parameters, in response to determining that a subsequent screening should be carried out,
select a recommended subsequent screening from among the plurality of subsequent screenings,
generate a first set of criteria for the recommended subsequent screening using the first set of parameters, the first set of criteria including at least one reagent to be added to a sample of the patient,
display results based on the first set of parameters, and
display the recommended subsequent screening.

19. The integrated method of screening of claim 16, further comprising:
carrying out the recommended subsequent screening.

20. A non-transitory computer program product, storing computer executable instructions which, when executed, perform the integrated method of screening of claim 16.

* * * * *